United States Patent
Singh et al.

(10) Patent No.: US 10,011,591 B2
(45) Date of Patent: Jul. 3, 2018

(54) CRYSTALLINE FORM OF AFATINIB DIMALEATE

(71) Applicant: Sun Pharmaceutical Industries Limited, Mumbai, Maharashtra (IN)

(72) Inventors: Shravan Kumar Singh, Mirzapur (IN); Shyam Sunder Verma, Varanasi (IN); Kaptan Singh, Gurgaon (IN); Mohan Prasad, Gurgaon (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 15/516,382

(22) PCT Filed: Oct. 1, 2015

(86) PCT No.: PCT/IB2015/057536
§ 371 (c)(1),
(2) Date: Mar. 31, 2017

(87) PCT Pub. No.: WO2016/051380
PCT Pub. Date: Apr. 7, 2016

(65) Prior Publication Data
US 2017/0240533 A1    Aug. 24, 2017

(30) Foreign Application Priority Data
Oct. 1, 2014 (IN) .......................... 2828/DEL/2014

(51) Int. Cl.
*C07D 405/12* (2006.01)

(52) U.S. Cl.
CPC ........ *C07D 405/12* (2013.01); *C07B 2200/13* (2013.01)

(58) Field of Classification Search
CPC .................................................. C07D 405/12
See application file for complete search history.

(56) References Cited

U.S. PATENT DOCUMENTS

| RE43,431 E | 5/2012 | Himmelsbach et al. | 514/266.22 |
| 8,426,586 B2 | 4/2013 | Soyka et al. ................. | 544/153 |
| 2005/0085495 A1* | 4/2005 | Soyka .................. | C07D 405/12 514/266.24 |
| 2014/0051713 A1* | 2/2014 | Gidwani .............. | C07D 405/12 514/266.24 |

FOREIGN PATENT DOCUMENTS

| CN | 104744445 | 7/2015 | ........... C07D 405/12 |
| WO | WO 2012/121764 | 9/2012 | ........... C07D 405/12 |
| WO | WO 2013/052157 | 4/2013 | ........... C07D 407/12 |
| WO | WO2013-052157 | * 11/2013 | ........... C07D 405/12 |
| WO | WO 2014/135876 | 9/2014 | ........... C07D 403/12 |
| WO | WO 2014/140989 | 9/2014 | ........... A61K 31/519 |

OTHER PUBLICATIONS

Co-pending PCT Application No. PCT/IB2015/057536 filed Oct. 1, 2015, published as WO 2016/051380 on Apr. 7, 2016.
International Search Report and Written Opinion for International Application No. PCT/IB2015/057536, issued by US/ISA dated Jan. 14, 2016.
International Preliminary Report on Patentability for International Application No. PCT/IB2015/057536, issued by WIPO dated Apr. 13, 2017.

* cited by examiner

*Primary Examiner* — Paul V Ward

(57) ABSTRACT

The present invention provides a crystalline Form I of afatinib dimaleate, its process for preparation and pharmaceutical composition thereof, and its use in the treatment of metastatic non-small cell lung cancer.

18 Claims, 3 Drawing Sheets

CRYSTALLINE FORM OF AFATINIB DIMALEATE

FIELD OF THE INVENTION

The present invention provides crystalline Form I of afatinib dimaleate, its process for preparation and pharmaceutical composition thereof, and its use in the treatment of metastatic non-small cell lung cancer.

BACKGROUND OF THE INVENTION

Afatinib dimaleate is a tyrosine kinase inhibitor, chemically designated as 2-butenamide, N-[4-[(3-chloro-4-fluorophenyl)amino]-7-[[(3S)-tetrahydro-3-furanyl]oxy]-6-quinazolinyl]-4-(dimethylamino)-,(2E)-, (2Z)-2-butenedioate (1:2) having the structure depicted by Formula I.

Formula I

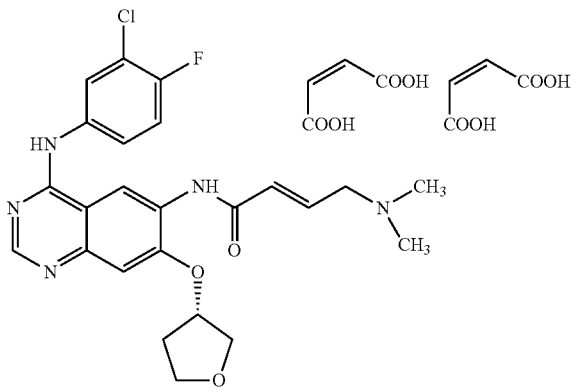

The discovery of new polymorphic forms of a compound is important in the development of pharmaceuticals, as these new forms may result in improved as ease of handling, ease of processing, storage stability, ease of purification, improved dissolution profile, and/or improved shelf-life.

U.S. Pat. No. 8,426,586 and PCT Publication Nos. WO 2012/121764 and WO 2013/052157 provide processes for the preparation of crystalline forms of afatinib and its salts.

SUMMARY OF THE INVENTION

The present invention relates to crystalline Form I of afatinib dimaleate, its preparation and pharmaceutical composition thereof, and its use in the treatment of metastatic non-small cell lung cancer.

The crystalline Form I of afatinib dimaleate of the present invention is highly pure, free-flowing, has good solubility, and prolonged shelf life. It is also stable towards polymorphic conversion and exhibits good bioavailability.

DETAILED DESCRIPTION OF THE INVENTION

The term "about," as used herein, refers to any value which lies within the range defined by a number up to ±10% of the value.

The term "triple layer package," as used herein, refers to the afatinib dimaleate being packed in a low density polyethylene (LDPE) pouch, then inserted and heat sealed under vacuum in a bag with a mixture of polyester/LDPE with silica sachet as a desiccant, and then further inserted and heat sealed under vacuum into an outer bag with a mixture of polyester film/aluminum foil/polyester LDPE.

A first aspect of the present invention provides crystalline Form I of afatinib dimaleate characterized by an X-ray powder diffraction (XRPD) pattern having peaks at d-spacings of about 4.9 and 3.4 Å.

The crystalline Form I of afatinib dimaleate is further characterized by an XRPD pattern having additional peaks at d-spacings of about 17.2, 8.0, 5.8, 4.3, and 3.6 Å.

The crystalline Form I of afatinib dimaleate is also characterized by an XRPD pattern having additional peaks at d-spacings of about 4.4, 4.2, 4.1, 3.5, 3.3, and 3.2 Å.

Table 1 summarizes the d-spacing values in Å, and the corresponding 2θ values, and the relative intensity of the crystalline Form I of afatinib dimaleate.

TABLE 1

| d-spacing [Å] | Position [±0.2° 2θ] | Relative Intensity [%] |
| --- | --- | --- |
| 17.2 | 5.1 | 100.0 |
| 9.8 | 9.0 | 9.0 |
| 8.0 | 11.0 | 17.2 |
| 7.9 | 11.1 | 15.8 |
| 7.0 | 12.6 | 9.1 |
| 6.5 | 13.6 | 9.8 |
| 5.8 | 15.3 | 22.7 |
| 5.3 | 16.7 | 14.7 |
| 5.1 | 17.4 | 26.6 |
| 4.9 | 18.0 | 42.4 |
| 4.7 | 18.7 | 26.9 |
| 4.6 | 19.0 | 26.7 |
| 4.5 | 19.7 | 23.7 |
| 4.4 | 20.2 | 35.2 |
| 4.3 | 20.7 | 48.3 |
| 4.2 | 20.9 | 43.2 |
| 4.1 | 21.7 | 33.1 |
| 4.0 | 22.2 | 26.9 |
| 3.8 | 23.2 | 24.2 |
| 3.7 | 23.8 | 29.1 |
| 3.6 | 24.8 | 60.9 |
| 3.5 | 25.3 | 58.6 |
| 3.4 | 25.8 | 68.7 |
| 3.3 | 26.6 | 57.2 |
| 3.2 | 27.1 | 53.0 |
| 3.1 | 28.1 | 32.6 |
| 3.0 | 29.6 | 29.1 |
| 2.8 | 31.6 | 21.4 |
| 2.6 | 33.3 | 24.1 |
| 2.5 | 36.1 | 17.6 |
| 2.4 | 37.0 | 16.4 |
| 2.3 | 38.6 | 15.4 |

Figure 1:
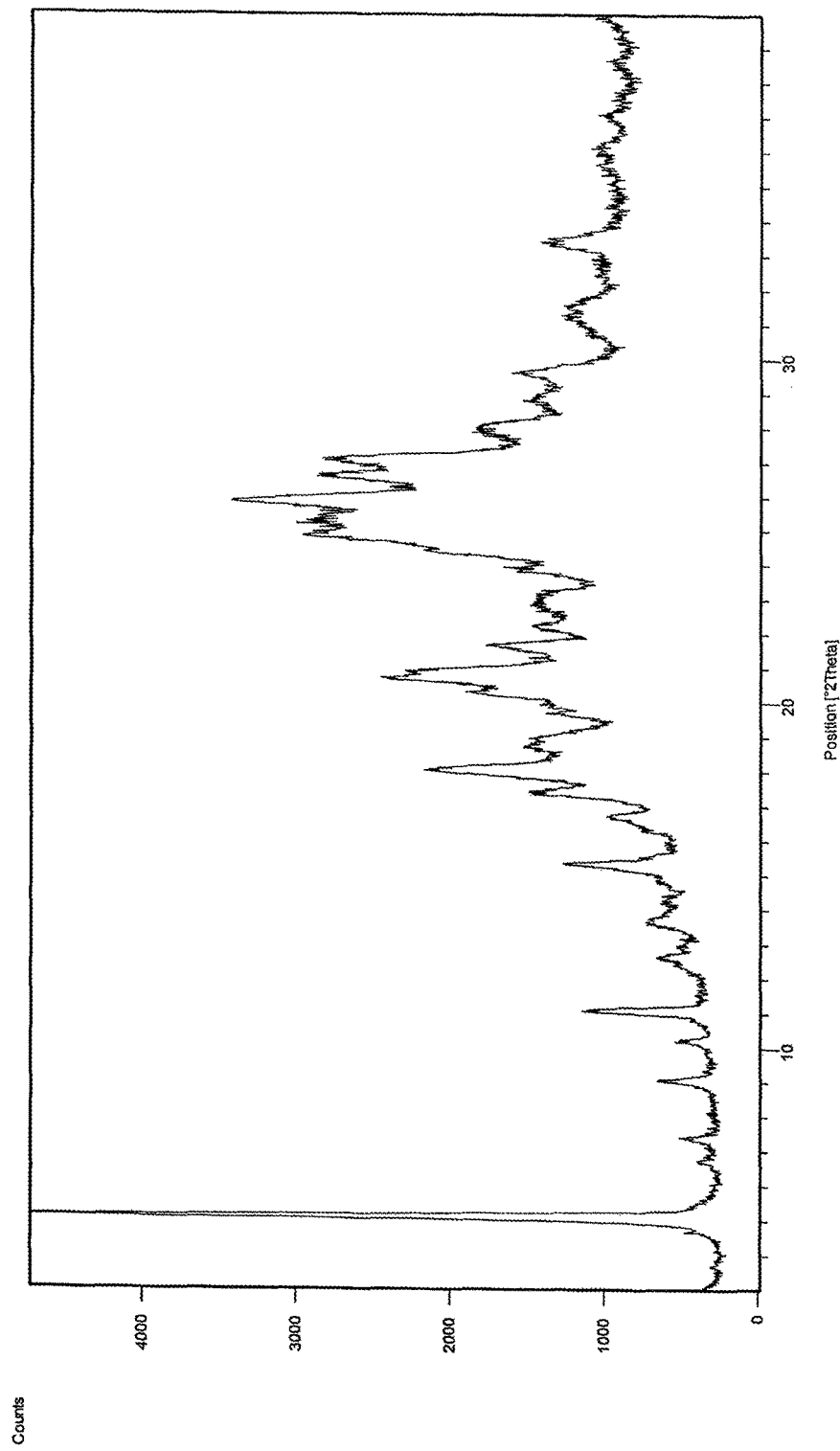
FIG. 1: X-ray powder diffraction (XRPD) pattern of the crystalline Form I of afatinib dimaleate.
Figure 2:
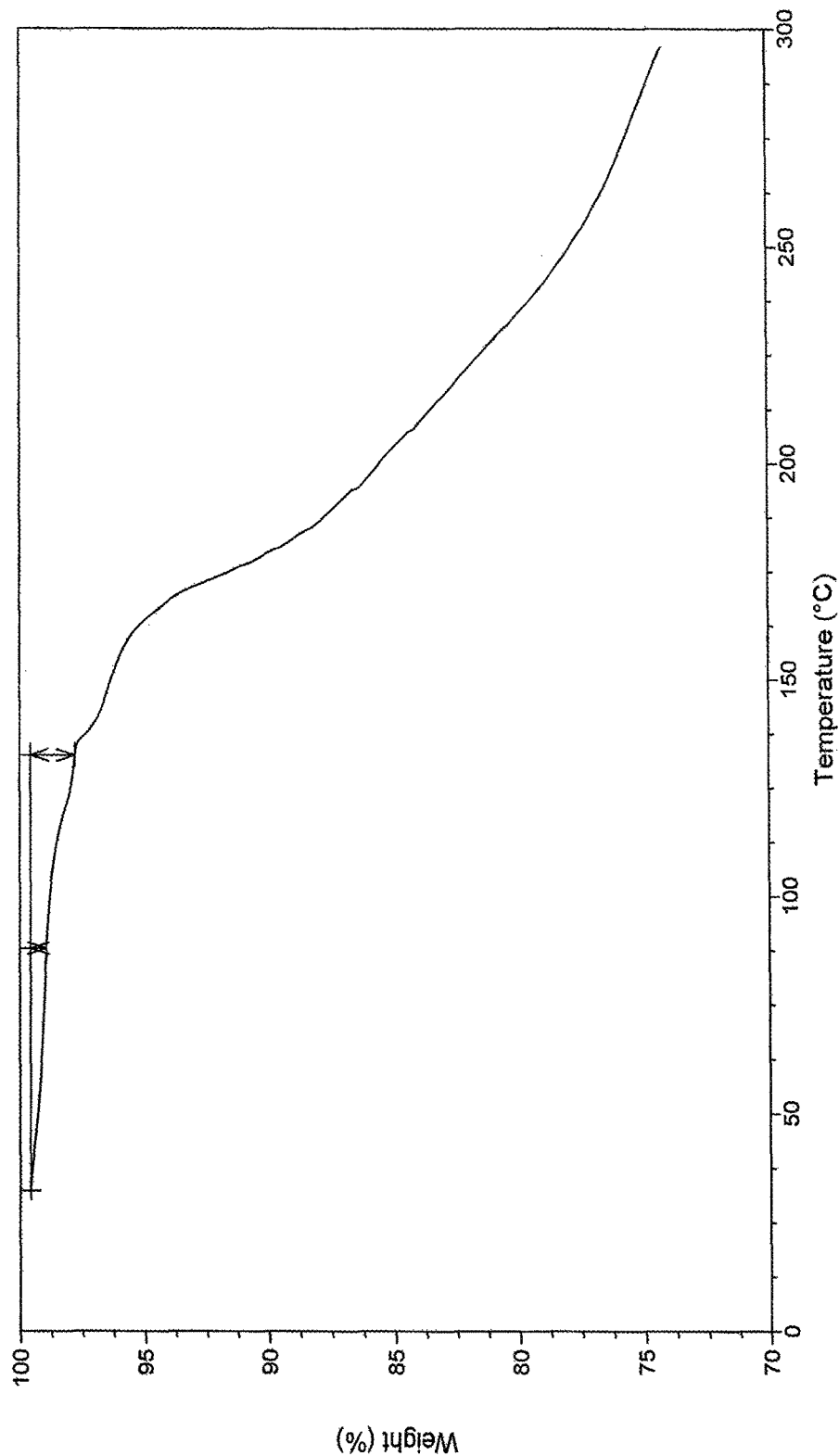
FIG. 2: Thermogravimetric Analysis thermogram of the crystalline Form I of afatinib dimaleate.
Figure 3:
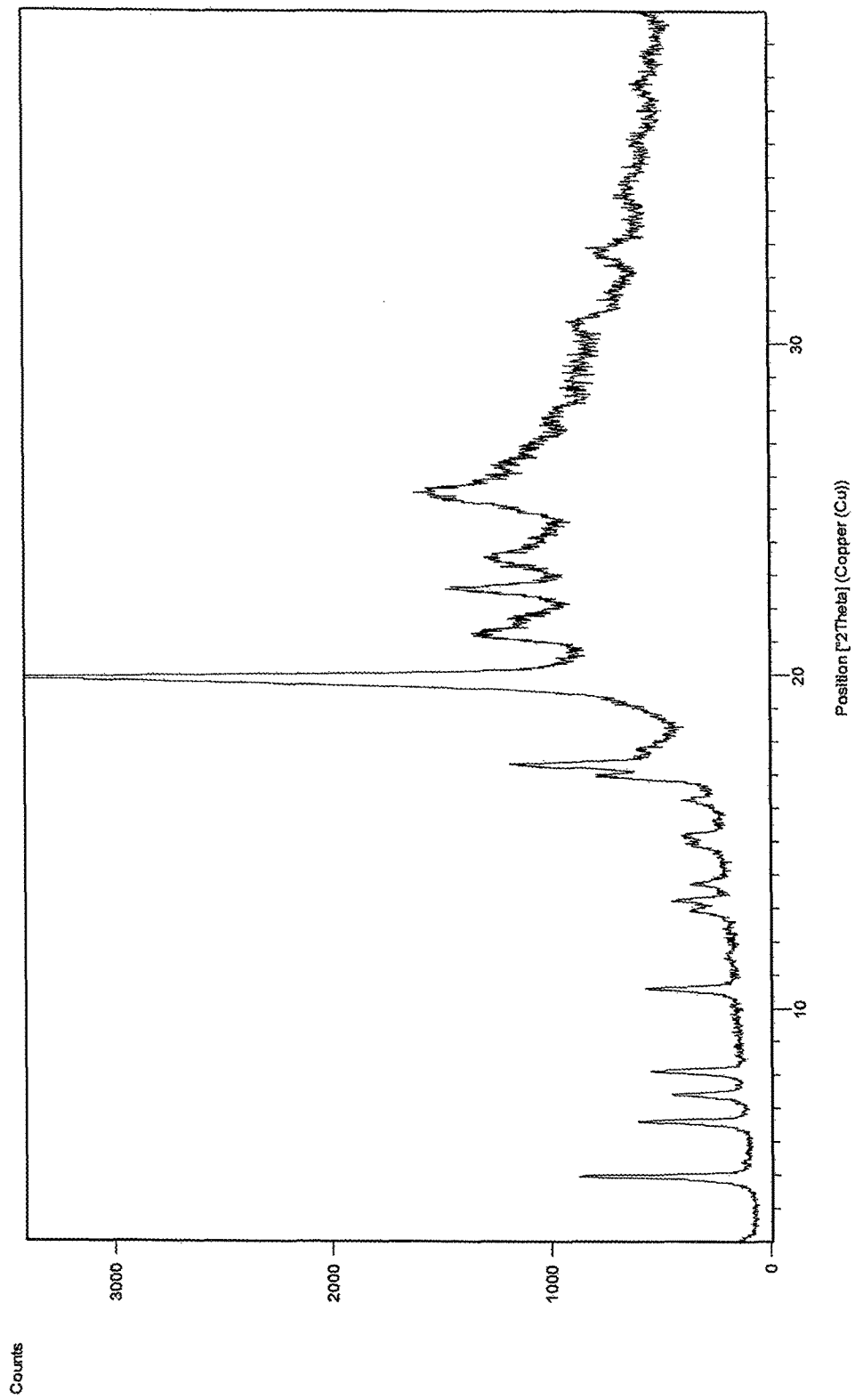
FIG. 3: XRPD pattern of crystalline Form A of afatinib dimaleate prepared as per Example 1 and as disclosed in PCT Publication No. WO 2013/052157.

Crystalline Form I of afatinib dimaleate is further characterized by an XRPD pattern and a TGA thermogram substantially as depicted in FIGS. 1 and 2, respectively.

A second aspect of the present invention provides a process for the preparation of crystalline Form I of afatinib dimaleate, characterized by an XRPD pattern having peaks at d-spacings of about 4.9 and 3.4 Å comprising:

i) dissolving afatinib dimaleate in an alcohol to obtain a solution;

ii) adding the solution of step i) to a polar aprotic solvent; and iii) isolating the crystalline Form I of afatinib dimaleate Afatinib dimaleate used as the starting material can be obtained by following the process as provided in Example 1 of the present invention or as described in U.S. Pat. No. 8,426,586.

A third aspect of the present invention provides a process for the preparation of a crystalline Form I of afatinib dimaleate characterized by an XRPD pattern having peaks at d-spacings of about 4.9 and 3.4 Å comprising:

i) dissolving afatinib base and maleic acid in an alcohol to obtain a solution;

ii) adding the solution of step i) to a polar aprotic solvent; and iii) isolating the crystalline Form I of afatinib dimaleate.

Afatinib base used as a starting material can be obtained by following the process as described in U.S. Pat. No. RE43,431.

The solution of afatinib dimaleate of step i) is obtained by suspending a crystalline form of afatinib dimaleate in an alcohol, or suspending afatinib and maleic acid in an alcohol, and stirring at a temperature of about 40° C. to about 80° C.

Examples of alcohol solvents include methanol, ethanol, 1-propanol, 1-butanol, 2-butanol, and mixtures thereof.

Examples of polar aprotic solvents include ethyl acetate, acetone, methyl isobutyl ketone, methyl ethyl ketone, acetonitrile, N,N-dimethylformamide, dimethylsulfoxide, tetrahydrofuran and mixtures thereof.

The solution of afatinib dimaleate of step i) is added to a polar aprotic solvent at a temperature of about 20° C. to about 40° C., and optionally stirred at a temperature of about 20° C. to about 40° C. for about 5 hours to about 24 hours, and further stirred at a temperature of about 0° C. to about 5° C. for about 1 hour to about 3 hours.

The isolation of crystalline Form I of afatinib dimaleate may be carried out by concentration, cooling, precipitation, washing, filtration, centrifugation, or combinations thereof, followed by drying using any suitable method, such as drying under reduced pressure, vacuum drying, or air drying.

Drying can be carried out at a temperature of about 35° C. to about 55° C. for about 10 hours to about 24 hours.

A fourth aspect of the present invention provides a pharmaceutical composition comprising crystalline Form I of afatinib dimaleate characterized by an XRPD pattern having peaks at d-spacings of about 4.9 and 3.4 Å and one or more pharmaceutically acceptable carriers, diluents, or excipients.

A fifth aspect of the present invention provides the use of crystalline Form I of afatinib dimaleate characterized by an XRPD pattern having peaks at d-spacings of about 4.9 and 3.4 Å for the first-line treatment of patients with metastatic non-small cell lung cancer whose tumors have an epidermal growth factor receptor exon 19 deletions or exon 21 (L858R) substitution mutations.

The crystalline Form I of afatinib dimaleate of present invention is a stable form. It is not converted to any other form of afatinib dimaleate when kept under storage conditions 25° C. ±2° C. and 60% ±5% relative humidity for two months under triple layer package.

While the present invention has been described in terms of its specific aspects and embodiments, certain modifications and equivalents will be apparent to those skilled in the art, and are intended to be included within the scope of the present invention.

Method

The X-ray diffraction patterns were recorded using a PANalytical® X'pert PRO with X'celerator® as the detector, 0.02 as step size, and 3-40° 2θ as range, using CuKα radiation.

The TGA was recorded using a TA Instruments® Q500.

The following examples are for illustrative purposes only and should not be construed as limiting the scope of the invention in any way.

EXAMPLES

Example 1

Preparation of a Crystalline Form A of Afatinib Dimaleate

In a round bottom flask, afatinib (20 g) was dissolved in methanol (200 mL) by stirring at 20° C. to 35° C. to obtain a solution. Maleic acid (9.5 g) was added to the solution at the same temperature to obtain a reaction mixture. The reaction mixture was heated and stirred at 55° C. to 60° C. for 30 minutes. The reaction mixture was concentrated under vacuum at 45° C. to 46° C. to obtain a solid. Cyclohexane (100 mL) was added to the solid and the mixture was stirred at 45° C. to 46° C. for 5 minutes. The solution was cooled to 20° C. to 30° C. to obtain a solid. The solid obtained was filtered and dried under vacuum at 40° C. to 45° C. to obtain the crystalline Form A of afatinib dimaleate.

Yield: 26.5 g

Example 2

Preparation of a Crystalline Form I of Afatinib Dimaleate

In a round bottom flask, crystalline Form A of afatinib dimaleate (5 g, as prepared in Example 1) was suspended in methanol (50 mL) and stirred at 60° C. to obtain a clear solution. The clear solution was added to ethyl acetate (100 mL) at 20° C. to 30° C. to obtain a reaction mixture. The reaction mixture was stirred at 20° C. to 30° C. for 18 hours. The reaction mixture was cooled to 0° C. to 5° C., and then stirred for 1.5 hours to obtain a solid. The solid was filtered, then washed with ethyl acetate (15 mL) under nitrogen atmosphere, and then dried under vacuum at 40° C. to 45° C. for 14 hours to obtain the crystalline Form I of afatinib dimaleate.

Yield: 2.5 g

Chromatographic purity: 99.9%

Example 3

Preparation of Crystalline Form I of Afatinib Dimaleate

In a round bottom flask, afatinib (5 g) and maleic acid (2.45 g) were suspended in methanol (70 mL) and stirred at 25° C. for 10 minutes. The reaction mixture was stirred at 60° C. to 65° C. for 45 minutes. Activated carbon (0.5 g) was added to the reaction mixture and the mixture was stirred at 60° C. to 65° C. for 30 minutes. The reaction mixture was filtered through a Hyflo® bed, and then washed with methanol (5 mL). The filtrate obtained was stirred at 60° C. for 20 minutes to obtain a clear solution. The clear solution obtained was added to ethyl acetate (150 mL) at 20° C. to 30° C. to obtain a reaction mixture. The reaction mixture was stirred at 20° C. to 30° C. for 5 hours. The reaction mixture was cooled to 0° C. to 5° C., and then stirred for 1.5 hours to obtain a solid. The solid was filtered, then washed with ethyl acetate (15 mL) under nitrogen atmosphere, and then dried under vacuum at 40° C. to 45° C. for 14 hours to obtain the crystalline Form I of afatinib dimaleate.

Yield: 4.8 g

Chromatographic purity: 99.78%

We Claim:

1. Crystalline Form I of afatinib dimaleate characterized by an X-ray Powder Diffraction pattern having diffraction peaks at d-spacings of about 17.2, 4.9 and 3.4 Å.

2. The crystalline Form I of afatinib dimaleate of claim 1, further characterized by an X-ray Powder Diffraction pattern having additional diffraction peaks at d-spacings of about 8.0, 5.8, 4.4, 4.3, 4.2, 4.1, 3.6, 3.5, 3.3, and 3.2 Å.

3. The crystalline Form I of afatinib dimaleate of claim 1, characterized by an X-ray Powder Diffraction pattern substantially as depicted in FIG. 1.

4. The crystalline Form I of afatinib dimaleate of claim 1, characterized by a Thermogravimetric Analysis thermogram substantially as depicted in FIG. 2.

5. A process for the preparation of the crystalline Form I of claim 1, comprising:
   i) dissolving afatinib dimaleate in an alcohol to obtain a solution;
   ii) adding the solution of step i) to a polar aprotic solvent; and
   iii) isolating the crystalline Form I of afatinib dimaleate.

6. A process for the preparation of the crystalline Form I of claim 1 comprising:
   i) dissolving afatinib and maleic acid in an alcohol to obtain a solution;
   ii) adding the solution of step i) to a polar aprotic solvent; and
   iii) isolating the crystalline Form I of afatinib dimaleate.

7. The process according to claim 5, wherein the alcohol is selected from methanol, ethanol, 1-propanol, 1-butanol, 2-butanol, or mixtures thereof.

8. The process according to claim 7, wherein the alcohol is methanol.

9. The process according to claim 5, wherein the polar aprotic solvent is selected from ethyl acetate, acetone, methyl isobutyl alcohol, methyl ethyl ketone, acetonitrile, N,N-dimethylformammide, dimethylsulfoxide, tetrahydrofuran, or mixtures thereof.

10. The process according to claim 9, wherein the polar aprotic solvent is ethyl acetate.

11. A pharmaceutical composition comprising the crystalline Form I of afatinib dimaleate of claim 1.

12. The pharmaceutical composition of claim 11 further comprising one or more pharmaceutically acceptable carriers, diluents, or excipients.

13. A method for first-line treatment of patients with metastatic non-small cell lung cancer whose tumors have an epidermal growth factor receptor exon 19 deletions or exon 21 (L858R) substitution mutations comprising administering to a patient in need thereof the crystalline Form 1 of afatinib dimaleate of claim 1.

14. A process for manufacturing a pharmaceutical composition comprising mixing the crystalline form I of afatinib dimaleate of claim 1 together with pharmaceutically acceptable carriers, diluents, and/or excipients.

15. The process according to claim 6, wherein the alcohol is selected from methanol, ethanol, 1-propanol, 1-butanol, 2-butanol, or mixtures thereof.

16. The process according to claim 15, wherein the alcohol is methanol.

17. The process according to claim 6, wherein the polar aprotic solvent is selected from ethyl acetate, acetone, methyl isobutyl alcohol, methyl ethyl ketone, acetonitrile, N,N-dimethylformammide, dimethylsulfoxide, tetrahydrofuran, or mixtures thereof.

18. The process according to claim 17, wherein the polar aprotic solvent is ethyl acetate.

* * * * *